United States Patent [19]
Dietlin et al.

[11] Patent Number: 6,028,222
[45] Date of Patent: Feb. 22, 2000

[54] STABLE LIQUID PARACETAMOL COMPOSITIONS, AND METHOD FOR PREPARING SAME

[75] Inventors: Francois Dietlin, Le Pecq; Daniele Fredj, Gif-sur-Yvette, both of France

[73] Assignee: SCR Pharmatop, France

[21] Appl. No.: 09/051,246

[22] PCT Filed: Aug. 5, 1997

[86] PCT No.: PCT/FR97/01452

§ 371 Date: Jun. 5, 1998

§ 102(e) Date: Jun. 5, 1998

[87] PCT Pub. No.: WO98/05314

PCT Pub. Date: Feb. 12, 1998

[30] Foreign Application Priority Data

Aug. 5, 1996 [FR] France ................................ 96 09858

[51] Int. Cl.⁷ .................................................. C07C 209/90
[52] U.S. Cl. .................................. 564/4; 514/617; 564/2; 564/5; 564/6; 564/7; 564/223
[58] Field of Search ................... 564/4, 5, 6, 7, 564/2, 223; 514/617

[56] References Cited

U.S. PATENT DOCUMENTS 4,727,064  2/1988  Pitha .......................................... 514/58
4,855,326  8/1989  Fuisz .......................................... 514/777
5,658,919  8/1997  Ratnaraj et al. ........................ 514/269

FOREIGN PATENT DOCUMENTS 9523595  9/1995  WIPO .

OTHER PUBLICATIONS

XP 002045737, 1995.
XP 002045739, 1985.
XP 002045740, 1983.
XP 002030816, 1986.

*Primary Examiner*—Shailendra Kumar
*Attorney, Agent, or Firm*—Bierman, Muserlian and Lucas

[57] ABSTRACT

Novel stable paracetamol compositions for use in therapeutic chemistry and specifically galenic pharmacy are disclosed. The compositions contain a solution of paracetamol in an aqueous solvent combined with a buffer having a pH of 4 to 8, and a free radical capturing agent. A water-insoluble inert gas is carefully bubbled through the aqueous solvent to remove oxygen from the medium. Said compositions may also be combined with a centrally or peripherally acting analgesic agent, and are provided as injectable compositions for relieving pain.

28 Claims, No Drawings

6,028,222

STABLE LIQUID PARACETAMOL COMPOSITIONS, AND METHOD FOR PREPARING SAME

This application is a 371 of PCT/FR97/01452, filed Aug. 5, 1997.

FIELD OF THE INVENTION

The present invention relates to novel stable, liquid, analgesic formulations, containing paracetamol as main active ingredient, either in combination or not, with an analgesic derivative.

DISCUSSION OF THE PRIOR ART

It has been known for many years and notably from a paper of FAIRBROTHER J. E. entitled: Acetaminophen, published in Analytical Profiles of Drug Substances (1974), volume 3, pp. 1–109, that paracetamol in the presence of moisture, and all the more in aqueous solution, may be hydrolysed to yield p-aminophenol, which compound may itself be broken down into quinone-imine. The rate of decomposition of paracetamol is enhanced as the temperature is increased and upon exposure to light.

In addition, the instability of paracetamol in aqueous solution as a function of the solution's pH has been extensively described. Thus, according to a paper entitled "Stability of aqueous solution of N-acetyl-p-aminophenol" (KOSHY K. T. and LACH J. I. J. *Pharm. Sci.*, 50 (1961), pp. 113–118), paracetamol in aqueous solution is unstable, a fact which primarily correlates with hydrolysis both in acidic and basic environment. This breakdown process is minimal at a pH close to 6, the half-life of the product thus degraded namely being as high as 21.8 years at 25° C.

According to Arrhenium law and knowing the specific reaction constant as determined by these authors, the time needed to observe a 5% decrease in paracetamol concentration of an aqueous solution stored at 25° C. at the optimal pH as been predicted to be 19 months. Besides hydrolysis, the paracetamol molecule separately undergoes another kind of decomposition that involves formation of a quinone-imine that may readily polymerize with generation of nitrogen-containing polymers.

These polymers and in particular those stemming from N-acetyl-p-benzoquinone-imine have been further described as being the toxic metabolite of paracetamol, which is endowed notably with cytotoxic and hemolytic effect. The decomposition of this metabolite in aqueous medium is still more complex and gives rise to p-benzoquinone and hydroquinone (D. DAHLIN, J. Med. Chem., 25 (1982), 885–886).

In the current state of the art and in view of the quality control requirements specific to pharmaceutical practice regulations, the stability of paracetamol in aqueous solutions is thus insufficient and does not allow the formulation of liquid pharmaceutical compositions for injection. As a result, the successful preparation of liquid pharmaceutical formulations for parenteral administration, based on paracetamol, has not been achieved.

A number of trials has been undertaken to slow down the decomposition of paracetamol in aqueous solution. Thus, in a paper entitled: Stabilization by ethylenediamine tetraacetic acid of amide and other groups in drug compound, (FOGG Q. G. and SUMMAN, A. M., *J. Clin. Pharm. Ther.*, 17: (1992), 107–109), it is stated that a 0.1% aqueous solution of paracetamol has a p-aminophen content resulting from hydrolysis of paracetamol, approximating 19,8% of the initial concentration of paracetamol, as observed after storage in the dark during 120 days. Addition of EDTA at a rate de 0.0075% brings down the decomposition rate to 7%. On the other hand, distilling an alkaline solution of paracetamol results in an ammonia concentration of 14%, in presence or not of 1000 ppm of ascorbic acid. Owing to its properties, ascorbic acid is indeed quite adapted to such stabilization. However, upon exposure to bright light, a paracetamol solution containing 1000 ppm of ascorbic acid does after all generate ammonia with a yield of 98%. In contrast, addition of EDTA (0.0075%) to such a solution cuts down decomposition rate, with an ammonia yield not higher than 14%.

Despite of such efforts, it has not been possible to prepare aqueous liquid solutions of paracetamol. In particular solutions for injection, having a guaranteed stability.

SUMMARY OF THE INVENTION

The present invention is aimed at solving the above stated problem in an appropriate manner. It is directed to stable pharmaceutical compositions of paracetamol in an aqueous solvent having added thereto a free radical antagonist. The aqueous solvent may be water or else aqueous mixtures containing water and a polyhydric compound such as polyethylene-glycol (PEG) 300, 400, 1000, 1540, 4000 or 8000, propylene glycol or tetraglycol. A water-soluble alcanol such as for example ethanol may also be used.

DETAILED DESCRIPTION OF THE INVENTION

Stability of the aqueous solutions mentioned above does not solely depend on the choice of a given carrier. It also depends on other variables, such as careful adjustment of pH, removal of oxygen dissolved in the carrier and addition of a free radical antagonist or a free radical scavenger.

Removal of dissolved oxygen is readily accomplished by bubbling an inert gas and preferably by bubbling nitrogen.

The appropriate free radical antagonist is chosen among the derivatives of ascorbic acid, those derivatives bearing at least a thiol functional group and straight chain or cyclic polyhydric compounds.

Preferred ascorbic acid derivatives are D- or L-ascorbic acid, an alkali metal ascorbate, an alkaline earth metal ascorbate or even still an aqueous medium-soluble ascorbic acid ester.

Free radical scavengers, bearing a thiol functional group may be an organic compound substituted by one or more thiol functional groups, of the aliphatic series such as cystein, acetylcystein, thioglycollic acid and salts thereof, thiolactic acid and salts thereof, dithlothreltol, reduced glutathion, thiourea, thioglycerol, methionine and mercaptoethane sulfonic acid.

The polyol used as a free radical scavenger is preferably a straight chain or a cyclic, polyhydroxy alcohol such as mannitol, sorbitol, inositol, isosorbide, glycerol, glucose and propylene-glycols.

Among free radical scavengers required pour stabilizing paracetamol, the ascorbic acid derivative currently preferred is sodium ascorbate. Preferred thiol functional group substituted derivatives are cystein, reduced-slate glutathion, N-acetylcystein and mercaptoethane sulfonic acid.

It may appear as convenient to combine several free radical scavengers as far as they are water-soluble and mutually compatible. Especially convenient free radical scavengers are mannitol, glucose, sorbitol or even glycerol. These may be readily combined.

It may appear as convenient to add to the preparation one or a number of complexing agents to improve stability of the molecule since the active ingredient is sensitive to the presence of trace metals that eventually speed up its decay.

Complexing agents are exemplified by nitrilotriacetic acid, ethylene diamino tetraacetic acid, ethylene diamino, N, N'-diacetic-N, N'-dipropionic acid, ethylene diamino tetraphosphonic acid, 2,2'-(ethylene diamino)dibutyric acid, or ethylene-glycol bis(diaminoethyl ether) N,N,N',N'-tetraacetic acid and sodium or calcium salts thereof.

The complexing agent also acts to complex bivalent ions (copper, zinc, calcium) that may be present and that have a negative influence of the aging of the formulation throughout storage.

The gas that is bubbled into the solution to drive out oxygen, may be nitrogen or carbon dioxide or still an inert gas. Nitrogen is favoured.

Isotonicity of the preparation may be achieved by adding an appropriate quantity of sodium chloride, glucose, levulose or postassium chloride, or calcium chloride, or calcium gluconoglucoheptonate, or mixtures thereof. The preferred isotonizing agent is sodium chloride.

The buffer used is a buffer compatible with parenteral administration in humans, the pH of which may be adjusted between 4 and 8. Preferred buffers are based on alkali metal ou alkaline earth metal acetates or phosphates. A more preferred buffer is sodium acetate/hydrogene phosphate adjusted to the required pH with hydrochloric acid or sodium hydroxide. The concentration of such a buffer may be comprised betwenn 0.1 and 10 mg/ml. The preferred concentration is confined in the range of 0.25 to 5 mg/ml.

On the other hand, preparations for injection have to be sterile and should lend themselves to heat treatment sterilization. It is known that in certain conditions, antioxidants such as glutathion are broken down ]FIALAIRC A. et al., *J. Pharm. Biomed. Anal.,* vol. 10, No 6, pp. 457–460 (1992)]. The breakdown of reduced glutathion during heat treatment sterilization ranges from 40 to 77% depending on the selected temperature conditions. During such sterilization procedures, it is convenient to employ means capable of preserving the integrity of these antioxidants. Addition of complexing agents to aqueous solutions inhibits thermal decomposition of thiol derivatives, such as glutathion.

Liquid pharmaceutical compositions according to the invention are preferably compositions intended for injection. The paracetamol content of the solution may range from 2 mg/ml to 50 mg/ml in case of so called dilute solutions, i.e. that can be directly infused by intravenous route and from 60 mg/ml to 350 mg/ml where so-called concentrated solution are considered, i.e. either intended for direct injection by intravenous or intramuscular route, or intended to be diluted prior to slow infusion administration. The preferred concentrations are comprised between 5 and 20 mg/ml for dilute solutions and between 100 and 250 mg/ml for concentrated solutions.

Pharmaceutical compositions according to the invention may further contain another active ingredient that enhances the specific effect of paracetamol.

In particular, the pharmaceutical compositions according to the invention may contain a CNS-acting analgesic such as for example a morphinic analgesic.

The morphinic analgesic is selected among the morphinic derivatives of natural, semi-synthetic or synthetic origin and piperidine derivatives selected from the following list, which is no way intended to be exhaustive: buprenorphine, dramadol, codeine, dextromoramide, dextropropoxyphene, hydrocodone, hydromorphone, ketobemidone, levomethadone, levorphanol, meptazinol, methadone, morphine, nalbuphine, nicomorphine, dizocine, diamorphine, dihydrocodeine, dipipanone, methorphane, dextromethorphane.

Preferred morphinic derivatives are codeine sulfate or morphine hydrochloride.

The codeine or codeine derivative concentration, expressed in terms of codeine base, is comprised between 0.2% and 25% in relation to the paracetamol content. The preferred codeine derivative is codeine sulfate. The concentration thereof is set between 0.5 and 15% in relation to the paracetamol content.

The morphine or morphine derivative concentration, expressed in terms of morphine base, is comprised between 0.05 and 5% in relation to the paracetamol content. The preferred morphine derivative is morphine hydrochloride the concentration of which is preferably set between 0.5 and 15% in relation to paracetamol content.

The compositions according to the invention may further have added thereto an anti-inflammatory agent such as of the of AINS type and in particular a phenylacetic acid compound. Such agents are exemplified by ketoprofen, flurbiprofen, tiaprofenic acid, niflumic acid, diclofenac or naproxen.

Compositions according to the invention may in addition incorporate an antiemetic either a CNS-acting neuroleptic such as haloperidol or chlorpromazine or metopimazine or of the gastrokinetic-mediated type such as metochlopramide or domperidone or even a serotoninergic agent.

Compositions in accordance with the invention may further incorporate an anti-epileptic drug such as sodium valproate, clonazepam, carbamazepine or phenytoin.

It may also be possible to combine paracetamol with a corticosteroid such as for example prednisone, prednisolone, methyl prednisone, dexamethasone, betametasone or an ester thereof.

Paracetamol can further be combined with a tricyclic antidepressant such as amitriptiline, imipramine, clomipramine.

Anti-inflammatory agents may be included in concentrations ranging from 0.100 g to 0.500 g per 1000 ml of formulated product.

In Case of Concentrated Solutions

The water content expressed in percentage is preferably in excess of 5% of the total volume and more preferably comprised between 10 and 65%.

The quantity of propylene glycol formulated in percentage is preferably in excess of 5% and more preferably comprised between 20 and 50%.

The PEG used is preferably PEG 300, PEG 400, PEG 1000, PEG 1540 or PEG 4000. Concentrations used are comprised between 10 and 60% in weight. PEG 300 and PEG 400 are further preferred. Preferred concentrations range from 20 to 60%.

Ethanol concentrations range from 0 to 30% of total volume and preferably range from 0 to 20%.

Tetraglycol concentrations used do not exceed 15% to allow for maximal quantities that can daily be received by parenteral administration viz 0.7 ml/kg of body weight.

Glycerol concentration varies from 0.5 to 5% as a function of the viscosity of the medium suitable for use depending on the administrative route.

In Case of Dilute Solutions

The quantity of water used given in percentage is preferably in excess of 20% of the total volume and preferably is comprised between 25 and 100%.

The quantity of propylene-glycol employed given in percentage is preferably comprised between 0 and 10%.

The PEG used is preferably PEG 300, PEG 400, or PEG 4000 with PEG 4000 being most preferred. Preferred concentrations range from 0 to 10%. Tetraglycol concentrations used do not exceed 5%. In preference, they are comprised between 0 and 4%.

The ascorbic acid or ascorbic acid derivative concentration which is used is preferably more than 0.05 mg/ml and more desirably, comprised between 0.15 mg/ml and 5 mg/ml. Higher quantities may indeed be used, without exceeding the solubility limits. Higher ascorbic acid or ascorbic acid derivative concentration are administered to human beings for prophylactic or therapeutic purposes.

Thiol derivative concentration is comprised between 0.001% and 30% and more desirably, comprised between 0.005% and 0.5% for dilute solutions, and between 0.1% and 20% for concentrated solutions.

The pH of the solution is desirably adjusted taking into consideration the optimal stability of paracetamol in aqueous solution, i.e. at a pH around 6.0.

The thus prepared composition may be packaged in glass sealed vials, or in stoppered glass vials or in bottles made of a polymer material such as polyethylene, or in soft material bags made from polyethylene, polyvinyl chloride or polypropylene.

The composition may be sterilized by heat treatment, for example at 121° C. during 20 minutes or else by sterile filtration.

Currently preferred compositions in accordance with the invention have the following ingredients:

Concentrated solutions

| Ingredient | Injection solution of paracetamol alone (per ml) | Injection solution of paracetamol associated to a morphinic compound (per ml) | |
|---|---|---|---|
| | | codeine | morphine |
| paracetamol | 0.160 g | 0.160 g | 0.160 g |
| codein sulfate.3H$_2$O | — | 0.0036 g | — |
| Morphine hydrochloride.3H$_2$O | — | — | 0.00037 |
| Propylene glycol | 0.270 ml | 0.270 ml | 0.270 ml |
| PEG 400 | 0.360 ml | 0.360 ml | 0.360 ml |
| Sodium acetate | 0.002 g | 0.002 g | 0.002 g |
| Reduced glutathion | 0.002 g | 0.002 g | 0.002 g |
| Hydrochloric acid 1 N | q.s. pH 6.0* | q.s. pH 6.0* | q.s. pH 6.0* |
| Water for injection | q.s. 1000 ml | q.s. 1000 ml | q.s. 1000 ml |
| Nitrogen | q.s.f. bubbling | q.s.f. bubbling | q.s.f. bubbling |

The pH specified above is the actual pH that has been measured by a pH-meter after obtaining a 5 fold dilution of the solution with distilled water. It will be noted that the apparent pH of the pure solution is different.

Using this solution composed of a solvent mixture constituted by 30% of propylene-glycol, by 40% of polyethylene-glycol 400 and by 30% of water (solution no 20), it is possible to dissolve about 200 mg/ml of paracetamol at 20° C. Choosing a concentration of 160 mg/ml allows one to be sure that no recristallization will occur, notably at low temperatures. In such situations, a volume of 6,25 ml of said solution contains 1000 mg of paracetamol.

Dilute solutions

| Ingredient | Injection solution of paracetamol alone (per ml) | solution of paracetamol associated to codein (per ml) | |
|---|---|---|---|
| | | Such morphinic compound is codein | Such morphinic compound is morphine |
| paracetamol | 0.0125 g | 0.125 g | 0.125 g |
| codein sulfate.3H$_2$O | — | 0.00018 g | — |
| Morphine hydrochloride.3H$_2$O | — | — | 0.000019 g |
| Mannitol | 0.025 g | 0.025 g | 0.025 g |
| Sodium hydrogen phosphate dihydrate | 0.0025 g | 0.00025 g | 000025 g |
| Sodium chloride | 0.002 g | 0.002 g | 0002 g |
| Disodium ethylene diamino tetraacetate | 0.0001 g | 0.0001 g | 0.0001 g |
| Hydrochloric acid or sodium hydroxide | q.s. pH 5.5 | q.s. pH 5.5 | q.s. pH 5.5 |
| Water for injection | q.s.f. 1000 ml | q.s.f. 1000 ml | q.s.f. 1000 ml |
| Nitrogen | q.s.f. bubbling | q.s.f. bubbling | q.s.f. bubbling |

The compositions according to the invention find therapeutic applications as pain relief drugs. For moderate pain, the solutions merely contain paracetamol. For acute pain, the solutions further contain a morphinic analgesic. Furthermore, the paracetamol solutions exert antipyretic activity.

The following examples are given by way of illustration and not by limitation.

EXAMPLE I

Determination of the Optimal Solvent Mixture 1.1 Concentrated solutions

Increasing quantities of paracetamol were introduced in the solvent mixtures. The dissolution rate of paracetamol increases with rise in temperature, so that the solubility tests in the individual media were run by heating the solvent mixture to 60° C. After dissolution was judged complete, the solutions were stored for 72 hours either at 25° C. or 4° C.

The solubility values are listed in the following table:

| Test n* | Water (ml) | Propylene-glycol (ml) | PEG 400 (ml) | Ethanol | Tetraglycol (ml) | Solubility at +4° C. (mg/ml) | Solubility at +25° C. (mg/ml) |
|---|---|---|---|---|---|---|---|
| 1  | 0.3  | 0.4  | 0.3  | —   | —    | 110  | 130  |
| 2  | 0.4  | 0.3  | 0.3  | —   | —    | 110  | 130  |
| 3  | 0.16 | 0.3  | 0.4  | —   | 0.15 | 190  | 230  |
| 4  | 0.5  | —    | 0.5  | —   | —    | 110  | 150  |
| 5  | 0.4  | 0.3  | 0.2  | 0.1 | —    | <110 | 120  |
| 6  | 0.5  | 0.3  | 0.1  | 0.1 | —    | <100 | 130  |
| 7  | 0.4  | 0.4  | 0.1  | 0.1 | —    | <100 | 150  |
| 8  | 0.5  | 0.3  | 0.2  | —   | —    | <100 | 120  |
| 9  | 0.6  | 0.3  | 0.2  | —   | —    | <100 | <100 |
| 10 | 0.5  | 0.4  | 0.1  | —   | —    | <100 | <100 |
| 11 | 0.55 | 0.3  | 0.05 | 0.1 | —    | <100 | <100 |
| 12 | 0.45 | 0.4  | 0.05 | 0.1 | —    | <100 | 120  |
| 13 | 0.65 | 0.3  | 0.05 | —   | —    | <100 | <100 |
| 14 | 0.55 | 0.3  | 0.05 | —   | —    | <100 | <100 |
| 15 | 0.4  | 0.4  | 0.2  | —   | —    | <100 | <150 |
| 16 | 0.45 | 0.45 | 0.1  | —   | —    | <100 | <100 |
| 17 | 0.4  | 0.2  | 0.4  | —   | —    | 160  | 200  |
| 18 | 0.5  | 0.2  | 0.3  | —   | —    | 160  | 160  |
| 19 | 0.5  | 0.1  | 0.3  | —   | —    | 100  | 190  |
| 20 | 0.3  | 0.3  | 0.4  | —   | —    | 190  | 200  |
| 21 | 0.3  | 0.3  | 0.35 | —   | 0.15 | 160  | 210  |
| 22 | 0.25 | 0.25 | 0.35 | —   | 0.15 | 170  | 220  |

The solubility values of the solvent mixtures do not increase in a consistent manner with increasing temperature. Solubility is not enhanced if ethanol is added.

In addition, due to oversaturation phenomena which are observed in such solutions, notably in media containing PEG, a delayed recristallization was noted subsequent to cooling. In these conditions, the solutions under study were kept for 14 days at 20° C., then there was added, to the solutions displaying no cristals following this time interval, a paracetamol germ cristal in order to elicit cristallization of potentially oversaturated solutions. Finally, it was found that solutions no 20 and no 3 have the highest solubility with respect to paracetamol, which threshold was comprised between 160 mg/ml and 170 mg/ml depending on temperature.

1.2 Dilute solutions

Paracetamol is quantities well exceeding the solubility threshold was introduced in the solvent mixtures previously warmed to 30° C. After stirring and cooling at 20° C., the solutions were filtered. The paracetamol content of these solutions was determined by reading the absorbance at 240 nm of a 1:200 dilution of the filtrate.

The results are recorded in the following tables.

| Type of solution (unless otherwise stated, the main solvent is distilled water) | concentration of paracetamol (mg/50 ml) |
|---|---|
| Water | 720 |
| 5% Glucose | 710 |
| 4.82% levulose | 730 |
| 7% mannitol | 680 |
| 5% sorbital | 685 |
| 0.9% sodium chloride | 615 |
| 10% Calcium gluconoglucoheptonate | 670 |
| Lestradet's solution (5% glucose, 0.2% sodium chloride, 0.15% potassium chloride, 1.1% calcium gluconoglucoheptonate) | 730 |
| Ringer's solution (0.7% sodium chloride, 0.1% potassium chloride, 0.1% sodium chloride) | 730 |
| Ringer's solution-Phosphate (0.7% sodium chloride, 0.182% monopotassium phosphate, 0.182% calcium chloride) | 710 |
| Ringer's solution-acetate (0.7% sodium chloride, 0.131% potassium acetate 0.013% calcium chloride) | 715 |
| Urea 0.3 M | 725 |
| Type of solution (the following solutions were prepared in Ringer's solution) | |
| Pure Ringer's solution | 735 |
| 4.0% PEG 4000 + 1.0% propylene-glycol + 0.5% ethanol | 905 |
| 4.0% PEG 4000 + 1.0% propylene-glycol + 1.0% ethanol | 905 |
| 4.0% PEG 4000 + 1.0% propylene-glycol + 2.0% ethanol | 930 |
| Type of solution (the following solutions were prepared in 0.9% sodium chloride solution) | |
| 0.9% sodium chloride | 615 |
| +0.6% tetraglycol | 640 |
| +1.2% tetraglycol | 680 |
| +3.0% tetraglycol | 720 |
| 1.0% PEG 4000 | 630 |
| 1.0% PEG 4000 + 0.6% tetraglycol | 660 |
| 1.0% PEG 4000 + 1.2% tetraglycol | 710 |
| 3.0% PEG 4000 + 2.0% tetraglycol | 950 |

Paracetamol solubility is increased by the presence of PEG.

Solubilities of paracetamol in mixtures of PEG 4000 and 0.9% sodium chloride solutions were determined in distilled water, at concentrations ranging from 0 to 7%, as a function of temperature.

The results are given in the following table:

| PEG 4000 concentration (%/vol.) in 0.9% sodium chloride solution | Solvent volume (ml) required to dissolve 1000 mg of paracetamol as a function of temperature | | | | |
| --- | --- | --- | --- | --- | --- |
| | 4° C. | 17° C. | 22° C. | 30° C. | 42° C. |
| 0% | 130 | 92 | 80 | 65 | 42 |
| 1% | 99 | 78 | 67 | 63 | 47 |
| 2% | 91 | 72 | 63 | 59 | 45 |
| 3% | 80 | 64 | 56 | 54 | 41 |
| 4% | 82 | 62 | 57 | 49 | 36 |
| 5% | 79 | 59 | 51 | 46 | 34 |
| 7% | 78 | 61 | 48 | 42 | 30 |

4.1 Concentrated solution

| Ingredient | Quantity | |
| --- | --- | --- |
| | Solution without nitrogen bubbling | solution subjected to nitrogen bubbling |
| Paracetamol | 0.160 g | 0.160 g |
| Propylene-glycol | 0.270 ml | 0.270 ml |
| PEG 400 | 0.360 ml | 0.360 ml |
| Sodium hydroxide or HCl 1N | q.s. pH 6.0 | q.s. pH 6.0 |
| Nitrogen | none | q.s.f. purging and filling |
| Water for injection | q.s.f 1000 ml | q.s.f. 1000 ml |

Solution 20 containing paracetamol in a quantity of 160 mg/ml, adjusted to pH 6.0 by sodium hydroxide or hydrochloric acid 1N, was either subjected or not subjected to nitrogen gas bubbling. Tightly stoppered and capped vials packed by dispensing 10 ml of such solutions under nitrogen atmosphere or air, were sterilized by autoclaving at 121° C. during 20 minutes. The percentage of secondary peaks was then measured by liquid chromatography with respect to the main peak of paracetamol, as well as was the pink color strength by reading the solution absorbance by absorption spectrophotometry at peak absorbance wavelength, that is 500 nm.

Results

| Solution tested | Secondary peaks in % of main peak of paracetamol | absorbance of the solution at 500 nm |
| --- | --- | --- |
| Autoclaved solution packed without nitrogen | 0.054 | 0.08 |
| Autoclaved solution packed under nitrogen | 0.036 | 0.03 |

It is therefore seen that the difference in color of the solution packed under nitrogen is very striking.

In order to check if 0% and 1% PEG-paracetamol solutions remain clear under cold storage, the following solutions ere prepared:

| Ingredient | Solution without PEG | Solution with PEG added |
| --- | --- | --- |
| Paracetamol | 1 g | 1 g |
| PEG 4000 | — | 1 g |
| 0.9% Sodium chloride solution in water for injection | q.s. 125 ml | q.s. 100 ml |

After storage of these solutions at 4° C. during 10 days, none of the vials tested showed cristallization. Presence of PEG is therefore not mandatory if the solutions are to remain clear throughout the time interval studied.

EXAMPLE II

Tests Conducted for Characterizing Paracetamol Breakdown in Solution 2.1 Demonstrating paracetamol instability in solution A paracetamol solution in water or in solution no 20 shows rapidly a pink color upon exposure to light or storage at high temperature. At 50° C., color development occurs in 2 weeks time. Appearance of such color tinge correlates with an increase in solution absorbance at a peak absorbance wavelength of 500 nm. According to the paper of Fairbrother mentioned above, exposure of paracetamol to moisture can result in hydrolysis with formation of para-aminophenol, followed by oxydation, with appearance of a pink color, typical of the production of quinoneimine.

2.2 Identifying the breakdown products of paracetamol

In aqueous or partially aqueous solutions, p-aminophenol is not detected during storage. Rapid production of colored products having a pink tinge is noted, the reaction rate being a function of temperature and light. In course of time, such derivatives are increasingly dark and evolutes to brown color.

All occurs as if, in contrast to what has been reported in the literature, the breakdown of paracetamol first involves an oxydative process followed by hydrolysis. According to this theory, paracetamol may react with an oxidant present in solution, for example oxygen dissolved in the aqueous layer. This mechanism may involve the production of free radicals resulting in molecular coupling, a fact that may account for the production of colored derivatives evoluting in color from pink to brown.

2.3 Tests for demonstrating inhibition of free radical production

A typical reaction involving the production of free radicals involves adding a 30% aqueous solution of hydrogen peroxide and a copper pentahydrate solution at a concentration of 62.5 mg/ml, to a 1.25% aqueous solution of paracetamol. In a matter of minutes, there develops a color reaction resulting in a color shift from yellow to dark brown. The color intensity observed decreases if free radical scavengers or glycerol are prior added to the paracetamol solution. Color intensity is a function of type of the type of free radical scavenger added, in the following decreasing order as judged by color intensity.

Paracetamol alone>paracetamol+N-acetylcystein>paracetamol+cystein>paracetamol+sorbitol>paracetamol+mannitol>paracetamol+glycerol.

EXAMPLE III

Stabilizing paracetamol solution by selecting the pH that allows maximal stability 3.1 Concentrated solution

| Ingredient | Quantity |
| --- | --- |
| Paracetamol | 0.160 g |
| Propylene-glycol | 0.270 ml |
| PEG 400 | 0.360 ml |
| Sodium hydroxide 1N or Hydrochloric acid 1N q.s.f. | pH 7.0–8.0–9.0–9.5–10.0 corresponding to actual pH: pH 5.8–6.7–7.1–7.5–8.0–8.5 |
| Nitrogen q.s.f. | purging and filling |
| Water for injection | q.s. 1000 ml |

Solution 20 containing paracetamol in a concentration of 160 mg/ml was adjusted to different pH's: the apparent pH is given in comparison to actual pH (between parenthesis) after a 5 fold-dilution: 7,0 (5,8)-8,0 (8,7)-8,5 (7,1)-9,0 (97,5)-9,5 (8,0)-10.0 (8,5) using a sodium hydroxide or normal hydrochloric acid solution. Vials that had been filled under nitrogen atmosphere by dispensing 10 ml of such solutions, tightly stoppered and capped, were sterilized by autoclaving at 121° C. for 20 minutes, and then in every case exposed, either to a temperature of 105° C. in the dark for 72 hours, or to a radiation of an actinic light at 5000° K. and 25° C. during 264 hours.

Results

After autoclaving, only the solution adjusted to pH 10 shows a pink tinge. After storage at 105° C. for 72 hours, absorbance at 500 nm as well as the concentration of breakdown products of paracetamol were minimal in the pH range from 7,5 to 9,5. Upon storage in the presence of light, the color strength is enhanced as the pH is increased. Color development is extremely weak at pH 7,0 (actual pH 5,8). Neither the paracetamol content, nor the breakdown products are affected by pH.

3.2 Diluted solution

| Ingredient | Quantity |
| --- | --- |
| Paracetamol | 0.008 g |
| Sodium chloride | 0.0067 g |
| Disodium phosphate dihydrate | 0.0012 g |
| 5% Citric acid q.s.f. | pH 5.0–6.0–7.0 |
| Nitrogen q.s.f. | bubbling and filling |
| Water for injection | q.s.f. 1000 ml |

The aqueous solution diluted and buffered having a paracetamol content of 8 mg/ml was adjusted to different pH values: pH 5,0–7,0 using a citric acid solution.

Vials that had been packed under nitrogen atmosphere by dispensing 10 ml of such solution, were tightly stoppered and capped, sterilized by autoclaving at 121° C. for 20 minutes, and then in every case exposed to 70° C. in the dark during 231 hours.

Results

Following autoclaving, only the solution adjusted to pH 7 shows a pink color. After storage, this same solution displays the brightest pink color. At pH 6,0 and 5,0 the solutions are faintly colored.

EXAMPLE IV

Stabilization of Paracetamol in Solution by Oxygen Removal Through Nitrogen Bubbling 4.2 Diluted solution Solution Tested

| | Quantity | |
| --- | --- | --- |
| Ingredient | Solution without nitrogen bubbling | solution subjected to nitrogen bubbling |
| Paracetamol | 0.008 g | 0.008 g |
| Sodium chloride | 0.008 g | 0.008 g |
| Disodium phosphate dihydrate | 000.1 g | 0.001 q |
| 5% Citric acid | q.s.f. pH 6.0 | q.s.f. pH 6.0 |
| Nitrogen | none | q.s.f. purging and filling |
| Water for injection | q.s.f. 1000 ml | q.s.f. 1000 ml |

The diluted aqueous solution containing paracetamol is adjusted to pH 6,0 by means of a citric acid solution.

Vials that had been filled under a nitrogen atmosphere by dispensing 10 ml of such solutions, were tightly stoppered and capped and then stored inside an incubator at 98° C. for 15 hours.

The percentage of secondary peaks in relation to the main peak of paracetamol was measured by liquid chromatography, so was the pink color strength by reading the solution absorbance by absorbance spectrophotometry at a peak absorption wavelength, that is 500 nm.

Results

| Solution tested | Secondary peaks in % of paracetamol main peak | Solution absorbance at 500 nm |
| --- | --- | --- |
| Solution packed without nitrogen atmosphere | 1.57 | 0.036 |
| solution packed under nitrogen atmosphere | 0.44 | 0.016 |

The pink color of the solution packed under nitrogen atmosphere is considerably tainter than that observed for the solution obtained after sterilization under nitrogen of the solution packed without nitrogen.

EXAMPLE V

Stabilizing Solutions of Paracetamol by Adding Free Radical Antagonists 5.1 Concentrated solution

| Ingredient | Quantity |
| --- | --- |
| Paracetamol | 0.160 g |
| Propylene-glycol | 0.270 ml |
| PEG 400 | 0.360 ml |
| Hydrochloric acid 1N or NaOH 1N q.s.f. | pH 6.0 |

-continued

| Ingredient | Quantity |
| --- | --- |
| Free radical scavenger (see quantitative results) | q.s.f. (see quantitative results) |
| Nitrogen q.s.f. | purging and filling |
| Water for injection | q.s.f 1000 ml |

The solutions thus prepared are divided in 10 ml capacity vials, stoppered with a Bromobutyl stopper and capped with an aluminium cap. After autoclaving at 121° C. for 20 minutes, the vials were stored for 48 hours, either in the presence of actinic light at 5500° K. at room temperature or at 70° C. in the dark. The preparation was examined for any change in color.

Results

| Free radical scavenger | Concentration | Appearance of the solution upon exposure to light Color intensity | Appearance of solution at 70° C. Color intensity |
| --- | --- | --- | --- |
| No scavenger | — | pink (+) | pink (++) |
| Sodium disulfite | 0.295 mg/ml | colorless | colorless |
| Sodium ascorbate | 1.0 mg/ml | yellow (+) | yellow (+) |
| Reduced glutathion | 1 mg/ml | colorless | colorless |
| Reduced glutathion | 8 mg/ml | colorless | colorless |
| Cystein hydrochloride | 1 mg/ml | cloudy | cloudy |
| α-monothioglycerol | 1 mg/ml | colorless | colorless |
| Dithiothreitol | 1 mg/ml | colorless | colorless |
| Mannitol | 50 mg/ml | colorless | colorless |

5.2 Dilute solution

Solutions tested

| | Quantity | | |
| --- | --- | --- | --- |
| Ingredient | Formulation A | Formulation B | Formulation C |
| Paracetamol | 0.008 g | 0.01 g | 0.0125 g |
| Sodium chloride | 0.008 g | 0.008 g | 0.00486 g |
| Disodium phosphate dihydrate or sodium acetate | 0.001 g | 0.001 g | 0.00125 g |
| Hydrochloric acid | q.s. pH 6.0 | q.s. pH 6.0 | q.s pH 5.5 |
| C.R.L. | q.s (see quantitative results) | | |
| Nitrogen q.s.f. | purging and filling | | |
| Water | q.s.f. 1000 ml | | |

The solutions thus prepared were divided in 10 ml, 100 ml or 80 ml capacity vials, stoppered with a Bromobutyl stopper and capped with an aluminium cap. The preparation was examined for any pink color development.

After autoclaving at 121° C. for 20 minutes, the vials were stored for 48 hours, either in the presence of actinic light at 5500° K. at room temperature or at 70° C. in the dark (formula A).

After autoclaving at 124° C. for 7 minutes, the vials were stored for 48 hours at room temperature in the dark (formulation B and C). The preparation was examined for any pink shift and the paracetamol as well as CRL were measured where a thiol derivative was used.

Results (CRL=free radical scavenger)

| C.R.L used | Concentration | Solution appearance upon exposure to light color | strength | Solution appearance at 70° C. color | strength |
| --- | --- | --- | --- | --- | --- |
| No C.R.L. | — | pink | (+) | pink | (++) |
| Thiourea | 0.5 mg/ml | colorless | | colorless | |
| Dithiothreitol | 1 mg/ml | colorless | | colorless | |
| α-monothioglycerol | 1 mg/ml | colorless | | colorless | |
| gluthathion | 1 mg/ml | colorless | | colorless | |
| Sodium ascorbate | 0.2 mg/ml | pink | (+) | pink | (+) |
| | 0.4 mg/ml | colorless | | yellow | (+) |
| | 0.6 mg/ml | pink | (+) | yellow | (+) |
| | 1.0 mg/ml | colorless | | yellow | (+) |
| Cystein hydrochloride | 0.05 mg/ml | colorless | | colorless | |
| | 0.1 mg/ml | colorless | | colorless | |
| | 0.25 mg/ml | colorless | | colorless | |
| | 0.5 mg/ml | colorless | | colorless | |
| | 0.75 mg/ml | colorless | | colorless | |
| | 1 mg/ml | colorless | | colorless | |
| | 2 mg/ml | colorless | | colorless | |
| | 5 mg/ml | colorless | | colorless | |

| C.R.L used | Concentration | Solution appearance color | strength | Dosages (in % of theoretical volume) C.R.L. | paracetamol |
| --- | --- | --- | --- | --- | --- |
| Cystein hydrochloride monohydrate | 0.2 mg/ml | colorless | | 80% | 99.2% |
| Cystein hydrochloride monohydrate | 0.5 mg/ml | colorless | | 95% | 99.6% |
| N-acetylcystein | 0.2 mg/ml | colorless | | 88% | 99.2% |
| Mannitol | 20 mg/ml | colorless | | | |
| Mannitol | 40 mg/ml | colorless | | | |
| Mannitol | 50 mg/ml | colorless | | | |
| Glucose | 50 mg/ml | colorless | | | |

EXAMPLE VI

Stabilization of Solutions of Paracetamol Containing a Morphinic Compound by Addition of a Free Radical Scavenger 6.1 Concentrated solution Solutions tested

| Ingredient | Quantity |
| --- | --- |
| Paracetamol | 0.160 g |
| Codein phosphate | 0.008 g |
| Propylene-glycol | 0.270 ml |
| PEG 400 | 0.360 ml |
| Hydrochloric acid 1N q.s. | q.s. pH 6.0 |
| Free radical scavenger | q.s. (see quantitative results) |
| Water for injection | q.s.f. 1000 ml |

The solutions thus prepared were divided in 10 ml capacity vials, stoppered with a Bromobutyl stopper and capped with a removable aluminium cap. After autoclaving at 121° C. for 20 minutes, the vials were stored for 48 hours either under actinic light at 5500° K. at room temperature, or at 70° C. in the dark. The preparation was inspected for any change in color.

Results

| Free radical scavenger | Concentration | Solution apperance upon exposure to light | | Solution apperance 70° C. | |
|---|---|---|---|---|---|
| | | color | strength | color | strength |
| No free radical scavenger | — | pink | (+) | pink | (++) |
| Sodium disulfite | 0.295 mg/ml | yellow | (+) | yellow | (++) |
| Sodium ascorbate | 1.0 mg/ml | yellow | (++) | yellow | (+++) |
| reduced glutathion | 1 mg/ml | yellow | (+) | amber yellow | (+++) |
| | 8 mg/ml | colorless | | yellow | (++) |
| | 16 mg/ml | colorless | | yellow | (+) |
| Dithio-threitol | 1 mg/ml | violet pink | (+++) | violet pink | (++++) |
| sodium hypo-phosphite | 5 mg/ml | pink | (+) | pink | (++) |

6.2 Dilute solutions

Solutions tested

| Ingredient | Quantity |
|---|---|
| Paracetamol | 0.008 g |
| Codein phosphate | 0.0004 g |
| Sodium chloride | 0.008 g |
| Disodium phosphate dihydrate | 0.0015 g |
| Hydrochloric acid | q.s.f. pH 6.0 |
| Free radical scavenger | q.s. (see results) |
| Nitrogen q.s.f. | purging and filling |
| Water for injection | q.s.f. 1000 ml |

The solutions thus prepared were divided in 10 ml capacity vials, stoppered with a Bromobutyl stopper and capped with an aluminium cap. After autoclaving at 121° C. for 20 minutes, the vials were stored for 48 hours, either under actinic light at 5500° C. at room temperature, or at 70° C. in the dark. The preparation was examined for any change in color.

For the solution not containing any free radical scavenger and for the solution containing 0.5 mg/ml of cystein hydrochloride as free radical antagonist, paracetamol as well as codein are measured by high performance liquid chromatography, immediately after autoclaving, in comparison with identical solutions not subjected to autoclaving.

Appearence scoring of the solutions

| Free radical scavenger | Concentration | Solution apperance upon exposure to light | | Solution apperance 70° C. | |
|---|---|---|---|---|---|
| | | color | strength | color | strength |
| No free radical scavenger | — | pink | (+) | pink | (+) |
| Sodium disulfite | 0.295 mg/ml | colorless | | colorless | |
| Dithio-threitol | 0.5 mg/ml | colorless | | colorless | |
| Monothio-glycerol | 0.5 mg/ml | grey | | grey | |
| Reduced glutathion | 2.0 mg/ml | colorless | | colorless | |
| N-acetylcystein | 2.0 mg/ml | grey | (+) | grey | (+) |
| Cystein hydrochloride | 0.05 mg/ml | colorless | | pink | (+) |
| | 0.1 mg/ml | colorless | | colorless | |
| | 0.25 mg/ml | colorless | | colorless | |
| | 0.5 mg/ml | colorless | | colorless | |
| | 0.75 mg/ml | colorless | | colorless | |
| | 1.0 mg/ml | colorless | | colorless | |
| | 2.0 mg/ml | colorless | | colorless | |
| | 5.0 mg/ml | colorless | | colorless | |

Assay results of paracetamol and codein

| Solution tested | Ingredient assayed | non sterilized solution | after sterilization |
|---|---|---|---|
| Solutions with no free radical scavenger added | paracetamol codein | 0.0078 g/ml 0.00043 g/ml | 0.0077 g/ml 0.00042 g/ml |
| Solution containing 0.5 mg/ml of cystein hydrochloride | paracetamol codein | 0.0082 g/ml 0.00042 g/ml | 0.0081 g/ml 0.00042 g/ml |

There is noted the lack of color development one one hand and excellent preservation of the active ingredients after heat treatment sterilization on the other hand.

EXAMPLE VII

Biological Tolerance to the Preparation 7.1 Hematological tolerance

Tested solutions

| Ingredient | Quantity |
|---|---|
| Paracetamol | 0.160 g |
| Propylene-glycol | 0.270 ml |
| PEC 400 | 0.360 ml |
| Nitrogen q.s.f. | purging and filling |
| Water for injection | q.s.f. 1000 ml |

The solution pH was not adjusted. The apparent pH is 7.6, corresponding to an actual pH of 6.5.

Whole human blood is incubated with the solution under study, in equal proportions by volume. 2 ml were drawn at 10 minutes intervals and centrifuged for 5 minutes at 5000 rpm. 100 µl of the supernatant were diluted in 1 ml of distilled water. The absorbance of this solution was determined against a water blank at 540 nm, peak absorption wavelength of hemoglobin.

The study was run in comparison with a negative control (physiological saline) and a positive control (pure water for injection).

Results

The absorbances of the individual solutions after different incubation periods are provided in the following table.

| Solution | T0 | 10 min | 20 min | 30 min | 40 min | 50 min | 60 min |
|---|---|---|---|---|---|---|---|
| Water p.p.i | 2.23 | 2.52 | 2.30 | 2.37 | 2.38 | 2.33 | 2.36 |
| Physiological saline | 0.04 | 0.05 | 0.05 | 0.05 | 0.04 | 0.05 | 0.04 |
| Sol. Tested | 0.09 | 0.19 | 0.27 | 0.25 | 0.24 | 0.24 | 0.25 |

7.2 Muscular tolerance
Solution tested

| Ingredient | Quantity |
|---|---|
| Paracetamol | 0.160 g |
| Propylene-glycol | 0.270 ml |
| PEG 400 | 0.360 ml |
| Nitrogen q.s.f. | purging and filling |
| Water for injection | q.s.f. 1000 ml |

The pH of this solution was not adjusted. Apparent pH is equal to 7,6.

Sprague-Dawley rats, weighing between 260 g and 450 g were anesthesized with an i.p. injection of ethyl carbamate (2 ml/kg of a 50% aqueous solution). The extensor digitorum longus muscle was dissected from the right or left hind leg, and placed in buffer medium having the following composition:

| Ingredient | Quantity |
|---|---|
| Sodium chloride | 6.8 g |
| Potassium chloride | 0.4 g |
| Dextrose | 1.0 g |
| Sodium bicarbonate | 2.2 g |
| Phenol red (sodium salt) | 0.005 g |
| Distilled water q.s.f. | 1 liter |
| Hydrochloric acid 1N q.s.f. | pH 7.4 |

The muscle is transiently fixed to a board and maintained in position by tendons. The test product was injected in an amount of 15 µl by means of a 25 µl-capacity Hamilton seringe no 702. The muscle is then placed over a grit and immersed in the buffer solution kept at 37° C. with carbogen bubbling throughout the incubation period. At 30 minutes intervals, the muscles were introduced in a tube containing fresh buffer at 37° C. The procedure was repeated 4 times. The buffer solution hence incubated is assayed for creatine kinase activity.

The study was run in parallel with:

muscle alone not subjected to injection (blank)

needle alone (introducing the needle without product injection)

physiological saline

Triton X-100 solution (negative controls)

solution 20 solution 20+paracetamol 160 mg/ml.

Creatine kinase was measured using a Hitachi 704 model analyzer in conjunction with a reagent kit sold under tradename high performance Enzyline CK NAC 10 (Biomerieux).

Results

The creatine kinase activity (IU/l) of the individual solutions after variable incubation periods are provided in the table given hereinafter:

| Solution tested | 30 min | 60 min | 90 min | 120 min | Total |
|---|---|---|---|---|---|
| Muscle alone | 23 ± 6 | 24 ± 12 | 15 ± 7 | 13 ± 5 | 75 |
| Needle alone | 35 ± 6 | 33 ± 10 | 20 ± 4 | 18 ± 7 | 106 |
| Physiological saline | 30 ± 6 | 10 ± 12 | 17 ± 6 | 23 ± 4 | 100 |
| Triton-X | 1802 ± 2114 | 1716 ± 978 | 155 ± 89 | 289 ± 251 | 14962 |
| Solution 20 (excipients) | 71 ± 24 | 89 ± 40 | 39 ± 27 | 62 ± 39 | 261 |
| Solution 20 + paracetamol | 141 ± 40 | 150 ± 60 | 68 ± 63 | 34 ± 24 | 393 |

No necrosis signs were recorded using the composition according to the invention as no significant difference between the results of test and excipient solutions was noted.

What is claimed is:

1. A stable, liquid formulation consisting essentially of acetaminophen dispersed in an aqueous medium containing a buffering agent and at least one member of the group consisting of a free radical scavenger and a radical antagonist.

2. The formulation of claim 1 wherein the aqueous medium has been deoxygenated by bubbling a water-insoluble inert gas.

3. The formulation of claim 1 wherein the aqueous medium is buffered at a pH of 4 to 8.

4. The formulation of claim 3 wherein the aqueous medium is buffered at a pH of 5.5 to 6.

5. The formulation of claim 1 containing a free radical antagonist selected from the group consisting of ascorbic acid ascorbic acid derivatives, organic compounds having at least one thiol and a alkyl polyhydroxylated and cycloalkyl polyhydroxylated compounds.

6. The formulation of claim 5 wherein the ascorbic acid derivatives ar selected from the group consisting of D-ascorbic acid, L-ascorbic acid, alkali metal ascorbates, alkaline earth metal ascorbates and water-soluble ascorbic acid esters.

7. The formulation of claim 5 wherein the organic compound having at least one thiol is aliphatic or cycloaliphatic.

8. The formulation of claim 1 containing a free radical scavenger containing at least one thiol is selected from the group consisting of thiolyglycolic acid, thiolacetic acid, dithiothreitol, reduced glutathion, thiourea, α-thioglycerol, cystein, acetlcystein and mercaptoethane sulfonic acid.

9. The formulation of claim 1 wherein the free radical scavenger is an aliphatic polyhydroxy alkanol of 2 to 10 carbon atoms.

10. The formulation of claim 9 wherein the polyhydroxy alkanol is a cyclic glucitol or a straight chain glucitol of 6 to 10 carbon atoms.

11. The formulation of claim 9 wherein the polyhydroxy alkanol is glycerol or propyleneglycol.

12. The formulation of claim 10 wherein the cyclic glucitol is selected from the group consisting of mannitol, sorbitol, inositol, glucose and levulose.

13. The formulation of claim 1 also containing at least one complexing agent.

14. The formulation of claim 1 wherein the acetaminophen has a concentration of 2 to 350 mg/ml.

15. The formulation of claim 14 wherein the concentration is 60 to 350 mg/ml.

16. The formulation of claim 14 diluted to a concentration of 2 to 50 mg/ml.

17. The formulation of claim 1 also containing an isotonizing agent in an amount to obtain isotonicity.

18. The formulation of claim 1 sterilized by heat treatment.

19. The formulation of claim 1 further containing an effective amount of an analgetic agent.

20. The formulation of claim 19 the analgetic agent is a morphine analgetic selected from the group consisting of natural morphines, semi-synthetic morphines, synthetic morphines, phenylpiperidines, nipecotic acid compounds, phenylcyclohexanol compounds and phenylazepine compounds.

21. The formulation of claim 20 having a concentration of acetaminophen is 0.05 to 5% by weight when morphine is present.

22. The formulation of claim 20 having an acetaminophen concentration of 0.2 to 2.5% by weight when codeine is present.

23. The formulation of claim 1 further containing an anti-inflammatory agent of the phenylacetic acid type.

24. The formulation of claim 23 wherein the anti-inflammatory agent is ketoprofen.

25. The formulation of claim 1 further containing an antiemetic agent.

26. The formulation of claim 1 further containing an antipileptic agent.

27. The formulation of claim 1 further containing a corticosteroid.

28. The formulation of claim 1 further containing a tricyclic antidepressant.

* * * * *

UNITED STATES PATENT AND TRADEMARK OFFICE
CERTIFICATE OF CORRECTION

PATENT NO. : 6,028,222
APPLICATION NO. : 09/051246
DATED : February 22, 2000
INVENTOR(S) : François Dietlin et al.

It is certified that error appears in the above-identified patent and that said Letters Patent is hereby corrected as shown below:

Column 1, line 21, "hydrolysed" should be -- hydrolyzed --

Column 1, line 35, "Arrenium" should be -- Arrhenius --

Column 1, line 67, "p-aminophen" should be -- p-aminophenol --

Column 2, line 1, "19,8%" should be -- 19.8% --

Column 2, lines 26-27, "alca-nol" should read -- alka-nol --

Column 2, line 50, "cystein, acetylcystein" should read -- cysteine, acetylcysteine --

Column 2, line 51, "dithlothritol" should read -- dithiothreitol --

Column 2, line 61, "cystein, reduced slate" should read -- cysteine, reduced state --

Column 2, line 62, "N-acetylcystein" should read -- N-acetylcysteine --

Column 3, line 27, "ou" should be -- or --

Column 3, line 28 "hydrogene" should be -- hydrogen --

Column 3, line 31 "betwenn" should be -- between --

Column 4, line 23, "AINS" should be -- NSAID --

Column 4, line 44, "1000 ml" should read -- 1.000 ml --

Column 5, line 47 (table), "codein" should read -- codeine --

Column 5, line 55 (table), "q.s. 1000 ml", all three occurrences, should be -- q.s. 1.000 ml --

Signed and Sealed this

Thirtieth Day of November, 2010

David J. Kappos
*Director of the United States Patent and Trademark Office*

Column 6, line 11, "recristallization" should read -- recrystallization --

Column 6, line 12, "6,25 ml" should read -- 6.25 ml --

Column 6, line 23 (table, column 3), "codein" should read -- codeine --

Column 6, line 24 (table), "codein sulfate" should read -- codeine sulfate --

Column 6, line 34 (table), next to last line, "q.s.f. 1000 ml", all three occurrences, should be --q.s.f. 1.000 ml --

Column 7, line 32, "recristallization" should read -- recrystallization --

Column 7, line 35, "cristals" should read -- crystals --

Column 7, line 36, "cristal" should read -- crystal --

Column 7, line 36, "cristallization" should read -- crystallization --

Column 7, line 44, "is" should read -- in --

Column 7, line 63, Table 1.2, "sorbital" should read -- sorbitol --

Column 9, Table 4.1, last line, "q.s.f. 1000 ml", should read -- q.s.f. 1.000 ml --

Column 10, line 12, "cristallization" should read -- crystallization --

Column 10, line 31, "oxydation" should read -- oxidation --

Column 10, line 44, "oxydative" should read -- oxidative --

Column 10, line 62, "of type of the type" should read -- of the type --

Column 10, line 66, "acetylcystein>paracetamol+cystein" should read
-- acetylcysteine>paracetamol+cysteine --

Column 11, line 16, in table 3.1, "q.s. 1000 ml" should read -- q.s. 1.000 ml --

Column 11, lines 21-22, "7,0 (5,8)-8,0 (8,7)-8,5 (7,1)-9,0 (97,5)-9,5 (8,0)-10,0 (8,5)" should read
-- 7.0 (5.8)-8.0 (8.7)-8.5 (7.1)-9.0 (7.5)-9.5 (8.0)-10.0 (8-5) --

Column 11, line 36, "7,5 to 9,5" should read -- 7.5 to 9.5 --

Column 11, line 38, "pH 7,0 (actual pH 5,8)" should read -- pH 7.0 (actual pH 5.8) --

Column 11, line 51, in table 3.2, "q.s.f. 1000 ml" should read -- q.s.f. 1.000 ml --

CERTIFICATE OF CORRECTION (continued)
U.S. Pat. No. 6,028,222

Column 11, line 56, "pH 5,0-7,0" should read -- pH 5.0-7.0 --

Column 11, line 66, "pH 6,0 and 5,0" should read -- pH 6.0 and 5.0 --

Column 12, line 20, in table 4.2, "q.s.f. 1000 ml", both occurrences, should read -- q.s.f. 1.000 ml --

Column 12, line 24, "pH 6,0" should read -- pH 6.0 --

Column 12, line 48, "tainter" should read -- fainter --

Column 13, line 8, in table 5.1, "q.s.f. 1000 ml" should read -- q.s.f. 1.000 ml --

Column 13, line 31, "cystein" should read -- cysteine --

Column 13, lines 50-51, in table 5.2, "q.s.f. 1000 ml" should read -- q.s.f. 1.000 ml --

Column 14, line 18 (in the table), "cystein" should read -- cysteine --

Column 14, line 31 (in the table), "cystein" should read -- cysteine --

Column 14, line 34 (in the table), "cystein" should read -- cysteine --

Column 14, line 37 (in the table), "acetylcystein" should read -- acetylcysteine --

Column 14, line 54 (in the table), "codein" should read -- codeine --

Column 14, line 59, in table 6.1, "q.s.f. 1000 ml" should read -- q.s.f. 1.000 ml --

Column 15, line 32, in the table, "codein" should read -- codeine --

Column 15, line 37, in table 6.2, "q.s.f. 1000 ml" should read -- q.s.f. 1.000 ml --

Column 15, line 47, "cystein" should read -- cysteine --

Column 15, line 49, "codein" should read -- codeine --

Column 16, line 12 (in the table), "acetylcystein" should read -- acetylcysteine --

Column 16, line 13 (in the table), "cystein" should read -- cysteine --

Column 16, line 21, "codein" should read -- codeine --

Column 16, line 27 (in the table), "codein" should read -- codeine --

Column 16, line 31 (in the table), "codein" should read -- codeine --

CERTIFICATE OF CORRECTION (continued)
U.S. Pat. No. 6,028,222

Column 16, line 32 (in the table), "cystein" should read -- cysteine --

Column 16, line 35, "one one hand" should read -- on one hand --

Column 16, line 53, in table 7.1, "q.s.f. 1000 ml" should read -- q.s.f. 1.000 ml --

Column 17, line 24, in table 7.2, "q.s.f. 1000 ml" should read -- q.s.f. 1.000 ml --

Column 17, line 28, "7,6" should read -- 7.6 --

Column 19, line 2, claim 6, "ar" should read -- are --

Column 19, line 12, claim 8, "cystein, acetlcystein" should read -- cysteine, acetylcysteine --

UNITED STATES PATENT AND TRADEMARK OFFICE
CERTIFICATE OF CORRECTION

PATENT NO. : 6,028,222 C1
APPLICATION NO. : 90/012606
DATED : March 16, 2015
INVENTOR(S) : Francois Dietlin It is certified that error appears in the above-identified patent and that said Letters Patent is hereby corrected as shown below:

Specification
- Column 1, line 45 of the Ex Parte Reexamination Certificate for U.S. Patent No. 6,028,222, "claim 53" should read "claim 37".

Signed and Sealed this
Twelfth Day of April, 2016

Michelle K. Lee
*Director of the United States Patent and Trademark Office*

(12) EX PARTE REEXAMINATION CERTIFICATE (10535th)
United States Patent
Dietlin et al.

(10) Number: US 6,028,222 C1
(45) Certificate Issued: Mar. 16, 2015

(54) STABLE LIQUID PARACETAMOL COMPOSITIONS, AND METHOD FOR PREPARING SAME

(75) Inventors: Francois Dietlin, Le Pecq (FR); Daniele Fredj, Gif-sur-Yvette (FR)

(73) Assignee: SCR Pharmatop, Le Chesnay (FR)

Reexamination Request:
No. 90/012,606, Sep. 14, 2012

Reexamination Certificate for:
Patent No.: 6,028,222
Issued: Feb. 22, 2000
Appl. No.: 09/051,246
PCT Filed: Aug. 5, 1997
PCT No.: PCT/FR97/01452
§ 371 (c)(1),
(2), (4) Date: Jun. 5, 1998
PCT Pub. No.: WO98/05314
PCT Pub. Date: Feb. 12, 1998

(30) Foreign Application Priority Data

Aug. 5, 1996 (FR) ...................................... 96 09858

(51) Int. Cl.
*A61K 31/167* (2006.01)
*A61K 31/485* (2006.01)
*A61K 47/02* (2006.01)
*A61K 47/10* (2006.01)
*A61K 47/12* (2006.01)
*A61K 47/16* (2006.01)
*A61K 47/18* (2006.01)
*A61K 47/20* (2006.01)
*A61K 47/22* (2006.01)
*A61K 9/00* (2006.01)
*A61K 31/165* (2006.01)

(52) U.S. Cl.
CPC ............. *A61K 9/0019* (2013.01); *A61K 31/167* (2013.01); *A61K 47/02* (2013.01); *A61K 31/485* (2013.01); *A61K 47/10* (2013.01); *A61K 47/12* (2013.01); *A61K 47/183* (2013.01); *A61K 47/20* (2013.01); *A61K 31/165* (2013.01); *A61K 47/22* (2013.01); *A61K 2300/00* (2013.01)
USPC ................ 564/4; 564/2; 564/5; 564/6; 564/7; 564/223

(58) Field of Classification Search
None
See application file for complete search history.

(56) References Cited

To view the complete listing of prior art documents cited during the proceeding for Reexamination Control Number 90/012,606, please refer to the USPTO's public Patent Application Information Retrieval (PAIR) system under the Display References tab.

*Primary Examiner* — Gary Kunz

(57) ABSTRACT

Novel stable paracetamol compositions for use in therapeutic chemistry and specifically galenic pharmacy are disclosed. The compositions contain a solution of paracetamol in an aqueous solvent combined with a buffer having a pH of 4 to 8, and a free radical capturing agent. A water-insoluble inert gas is carefully bubbled through the aqueous solvent to remove oxygen from the medium. Said compositions may also be combined with a centrally or peripherally acting analgesic agent, and are provided as injectable compositions for relieving pain.

Attention is directed to the decision of *Cadence Pharmaceuticals, Inc. et al* v. *Exela Pharma Sciences, Llc. et al.* in *U.S. District Court of Delaware; 1:11Cv733 filed 8/18/11*, Court found infringement and validity of patents on 5/9/13 relating to this patent. This reexamination may not have resolved all questions raised by this decision. See 37 CFR 1.552(c) for *ex parte* reexamination and 37 CFR 1.906(c) for *inter partes* reexamination.

US 6,028,222 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 5, 8-12 and 14-16 are cancelled.

Claims 1, 6, 7, 21 and 22 are determined to be patentable as amended.

Claims 2-4, 13 and 17-19, dependent on an amended claim, are determined to be patentable.

New claims 29-48 are added and determined to be patentable.

Claims 20 and 23-28 were not reexamined.

1. A stable, liquid formulation *for intravenous administration* consisting essentially of acetaminophen dispersed in an aqueous medium containing a buffering agent and at least one member of the group consisting of a free radical scavenger and a *free* radical antagonist,
    wherein the at least one member is selected from the group consisting of ascorbic acid, ascorbic acid derivatives, thioglycolic acid, thiolactic acid, dithiothreitol, reduced glutathione, thiourea, α-thioglycerol, cysteine, acetylcysteine, mercaptoethane sulfonic acid, mannitol, sorbitol, inositol, glucose, levulose, glycerol, *and propylene glycol; and*
    *wherein the formulation has an acetaminophen concentration of 5 mg/mL to 20 mg/mL.*

6. The formulation of claim [5] *1* wherein the ascorbic acid derivatives are selected from the group consisting of D-ascorbic acid, L-ascorbic acid, alkali metal ascorbates, alkaline earth metal ascorbates and water-soluble ascorbic acid esters.

7. The formulation of claim [5] *53* wherein the organic compound having at least one thiol is aliphatic or cycloaliphatic.

21. The formulation of claim 20 [having a concentration of acetaminophen is 0.05 to 5% by weight when] *wherein the analgetic agent is* morphine [is present].

22. The formulation of claim 20 [having an acetaminophen concentration of 0.2 to 2.5% by weight when] *wherein the analgetic agent is* codeine [is present].

29. *A stable, isotonic, liquid formulation of acetaminophen for intravenous administration consisting essentially of acetaminophen dispersed in a deoxygenated aqueous medium containing a buffering agent and at least one member of the group consisting of a free radical scavenger and a radical antagonist, wherein the at least one member of the group consisting of a free radical scavenger and a radical antagonist is selected from the group consisting of mannitol and cysteine hydrochloride, wherein the aqueous medium is a mixture of water and a polyhydric compound or a water-soluble alkanol, the pH is 5.5 to 6, and the concentration of acetaminophen is 2 to 20 mg/mL.*

30. *The formulation of claim 1, wherein the acetaminophen concentration is 10 mg/mL.*

31. *The formulation of claim 1, wherein the aqueous medium is selected from the group consisting of water, a mixture of water and a polyhydric compound, and a mixture of water and a water-soluble alkanol.*

32. *The formulation of claim 31, wherein the aqueous medium is water.*

33. *The formulation of claim 1, wherein the at least one member is cysteine.*

34. *The formulation of claim 1, wherein the at least one member is mannitol.*

35. *The formulation of claim 17, wherein the isotonizing agent is selected from the group consisting of sodium chloride, glucose, levulose, potassium chloride, calcium chloride, calcium gluconoglucoheptonate, and mixtures thereof.*

36. *The formulation of claim 1, wherein the formulation is sterilized, and wherein the sterilization does not degrade the at least one member.*

37. *A stable, liquid formulation for intravenous administration consisting essentially of acetaminophen dispersed in an aqueous medium containing a buffering agent and at least one member of the group consisting of a free radical scavenger and a free radical antagonist,*
    *wherein the at least one member is selected from the group consisting of ascorbic acid, ascorbic acid derivatives, organic compounds having at least one thiol, alkyl polyhydroxylated compounds, and cycloalkyl polyhydroxylated compounds,*
    *wherein the aqueous medium is water, and*
    *wherein the formulation has an acetaminophen concentration of 5 mg/mL to 20 mg/mL.*

38. *The formulation of claim 37, wherein the acetaminophen concentration is 10 mg/mL.*

39. *The formulation of claim 37, wherein the formulation has a pH of 4 to 8.*

40. *The formulation of claim 37, wherein the formulation contains an isotonizing agent selected from the group consisting of sodium chloride, glucose, levulose, potassium chloride, calcium chloride, calcium gluconoglucoheptonate, and mixtures thereof.*

41. *The formulation of claim 37, wherein the formulation is sterilized by heat treatment, and wherein the sterilization does not degrade the at least one member.*

42. *The formulation of claim 37, wherein the at least one member is cysteine.*

43. *The formulation of claim 37, wherein the at least one member is mannitol.*

44. *A stable, liquid formulation for intravenous administration consisting essentially of acetaminophen dispersed in an aqueous medium containing a buffering agent and at least one member of the group consisting of a free radical scavenger and a free radical antagonist,*
    *wherein the at least one member is selected from the group consisting of ascorbic acid, ascorbic acid derivatives, thioglycolic acid, thiolactic acid, dithiothreitol, reduced glutathione, thiourea, α-thioglycerol, cysteine, acetylcysteine, mercaptoethane sulfonic acid, mannitol, sorbitol, inositol, glucose, levulose, glycerol, and propylene glycol,*
    *wherein the aqueous medium is water, and*
    *wherein the formulation has an acetaminophen concentration of 5 mg/mL to 20 mg/mL.*

45. *The formulation of claim 44, wherein the acetaminophen concentration is 10 mg/mL.*

46. *The formulation of claim 44, wherein the formulation has a pH of 4 to 8.*

47. *The formulation of claim 44, wherein the formulation contains an isotonizing agent selected from the group con-* sisting of sodium chloride, glucose, levulose, potassium chloride, calcium chloride, calcium gluconoglucoheptonate, and mixtures thereof.

48. The formulation of claim 37, wherein the alkyl or cyclo alkyl polyhydroxylated compounds are selected from the group consisting of mannitol, sorbitol, glucose, and glycerol.

\* \* \* \* \*